United States Patent [19]

Martin

[11] Patent Number: 5,662,891
[45] Date of Patent: Sep. 2, 1997

[54] NAIL COATING COMPOSITON FREE OF AROMATIC AND KETONE SOLVENTS AND FORMALDEHYDE RESINS

[75] Inventor: Frederick L. Martin, St. John, Ind.

[73] Assignee: Almell, Ltd., Dallas, Tex.

[21] Appl. No.: 580,153

[22] Filed: Dec. 28, 1995

[51] Int. Cl.$^6$ .................................................. A61K 7/043
[52] U.S. Cl. ................................ 424/61; 524/31; 524/499
[58] Field of Search .............................. 424/61; 524/31, 524/499

[56] References Cited

U.S. PATENT DOCUMENTS

| | | | |
|---|---|---|---|
| 2,173,755 | 5/1936 | Fuller | 167/85 |
| 2,824,098 | 2/1958 | Volberg et al. | 260/230 |
| 4,097,589 | 6/1978 | Shansky | 424/61 |
| 4,179,304 | 12/1979 | Rossomando | 106/177 |
| 4,229,227 | 10/1980 | Ikeda et al. | 106/181 |
| 4,301,046 | 11/1981 | Schlossman | 260/16 |
| 4,409,203 | 10/1983 | Gordon et al. | 424/61 |
| 4,421,881 | 12/1983 | Benkendorf et al. | 524/24 |
| 4,649,045 | 3/1987 | Gaske et al. | 424/61 |
| 4,712,571 | 12/1987 | Remz et al. | 132/88.7 |
| 4,740,370 | 4/1988 | Faryniarz et al. | 424/61 |
| 4,822,423 | 4/1989 | Soyama et al. | 424/61 |
| 5,227,155 | 7/1993 | Castrogiovanni et al. | 424/61 |
| 5,512,273 | 4/1996 | Martin | 424/61 |

FOREIGN PATENT DOCUMENTS

| | | |
|---|---|---|
| 0336193 | 10/1989 | European Pat. Off. . |
| 62-111909 | 5/1987 | Japan . |

OTHER PUBLICATIONS

Baran and Mailbach; *Cosmetics Dermatology* 1st Editon, 1994; Martin Dunitz, Ltd., London, U.K., "Nail Varnish" pp. 151–156.

Schlossman, "Manicure Preparations", *Poucher's Perfumes, Cosmetics and Soaps*, vol. 3, Cosmetics, Ninth Edition, 1993; Chapman & Hall, London, U.K., pp. 244–258.

"Decorative Cosmetic", *Handbook of Cosmetics Science and Technology*, 1st Edition, 1993, Elsevier Science Publishers, Ltd., Oxford, U.K., pp. 121, 160–164.

Schlossman, "Trends in nail care technology", *Cosmetics & Toiletries*, vol. 96, pp. 51–54 (Apr. 1981).

Schlossman, "Nail polish colorants", *Cosmetics & Toiletries* vol. 95, pp. 31–33 (Jan. 1980).

Wimmer and Shlossman, "The History of Nail Polish", *Cosmetics & Toiletries*, vol. 107, pp. 115–120, (Sep. 1992).

16th IFSCC Congress, "The Effect of Toluene on the Properties of Suspension Nail Polish", vol. 2, pp. 18–30 (1990).

Schlossman, "Modern nail enamel technology", *J. Soc. Cosmet. Chem.*, vol. 31, pp. 29–36 (Jan./Feb. 1980).

Schlossman and Wimmer, "Advances in nail enamel technology", *J.Soc. Cosmet. Chem.*, vol. 43, pp. 331–337 (Nov./Dec. 1992).

Schlossman and Khamis, "Lower VOC Nailpolish Removers", DCI/Oct. 1992, pp. 32, 38, 40, 95.

Schlossman, "Formulating Ethnic Makeup Products", *Cosmetics & Toiletries*, vol. 110, pp. 59–63, (Oct. 1995).

Peirano, "Other film formers for nail enamels", *American Perfumer and Cosmetics*, vol. 84, pp. 35–36, (Aug. 1969).

Periano, "Nail Lacquers and Removers", *Cosmetics Science and Technology*, Interscience Publishers, Inc., pp. 678–692 1957.

Schlossman, "Nail-enamel resins", *Cosmetic Technology*, pp. 53–55, (Oct. 1979).

Scher, "Clearing Up a Rash Comes from Uncovering Its Cause", *NAILS*, pp. 86, 88, (Oct. 1995).

"Nailing Down the Best Polish", *Consumer Reports*, pp. 104–107, (Feb. 1995).

Advertisement by Seche Vite, "What Makes a 'Professional' Product *Professional?*", date unknown.

*Primary Examiner*—Robert E. Sellers
*Attorney, Agent, or Firm*—Sidley & Austin

[57] ABSTRACT

A nail coating composition, which is substantially free to totally free of aromatic solvents, ketones, and formaldehyde containing resins, includes nitrocellulose, maleic modified rosin based resin, and polyester resin as the film forming polymers; sucrose acetate isobutyrate, butyl benzyl phthalate, and glyceryl tribenzoate as the plasticizers; at least one vitamin; at least one UV blocking agent; at least one protein; at least one moisturizer; at least one smoothing agent; at least one adhesion promoter; and a mixture of solvents, wherein all of the solvents in the composition are selected from the group consisting of alkanes having 4 to 10 carbon atoms, aliphatic esters having 3 to 10 carbon atoms, alkanols having 2 to 10 carbon atoms, cycloalkanes having 4 to 10 carbon atoms, cycloaliphatic esters having 4 to 10 carbon atoms, cycloalkanols having 4 to 10 carbon atoms, and mixtures of any two or more thereof.

20 Claims, No Drawings

NAIL COATING COMPOSITON FREE OF AROMATIC AND KETONE SOLVENTS AND FORMALDEHYDE RESINS

FIELD OF THE INVENTION

The invention relates to a composition which can be applied to fingernails or toenails.

BACKGROUND OF THE INVENTION

Nail polish is generally applied to fingernails or toenails as two or more layers, for example in the form of a base coat layer, one or more pigmented layers, and a top coat. It is generally desirable for each applied coat to be completely dry before the application of the next coat. However, as such sequentially achieved drying time substantially increases the total time required for a multi-coat application, it is desirable to be able to apply a secondary coat to the base coat before the base coat is completely dry. However, if the base coat dries too slowly after the application of the secondary coat, the base coat solvents can be trapped at the interface between the secondary coat and the previously applied base coat, reducing the cohesiveness of the previously applied base coat and the adherence of the secondary coat to the previously applied base coat. Thus it is desirable to provide a base coat wherein each of the solvents in the base coat can evaporate from the base coat within a reasonably short period of time and not be trapped by a secondary coat.

It has been a common practice to employ aromatic solvents, such as toluene, as one of the solvents in a nail coating composition. However, the use of toluene is now considered to be undesirable because it is toxic by ingestion, inhalation, or skin absorption, and may cause mild macrocytic anemia. Many of the solvents employed in nail coating compositions are considered to have a drying effect on human skin and nails when there is prolonged contact. Thus, it is desirable that a nail coating composition avoid the use of aromatic solvents, such as toluene, as well as provide protection against such drying effects of the solvents which are used.

Pappas et al, U.S. Pat. No. 5,206,011, discusses the prior art solvent mixtures for nail enamels and concludes that the complicated character of the nail enamel mixtures of the prior art and the many possible combinations of volatile and nonvolatile components had, until the Pappas et al discovery, made the determination of a proper solvent balance from the perspective of viscosity, solubility of the individual components and the acceptability of the deposited enamel (gloss) in combination with a drying time of less than three minutes virtually impossible. Pappas et al state that prior to their discovery, the identification of the evaporation rates of the individual solvents under various conditions had not removed the uncertainty involved in determining a suitable solvent balance incorporating quick-drying characteristics. Although the desirability of a quick-drying nail enamel had been a long-felt need, the rate of drying of the nail enamels of the prior art had been limited by these considerations. Pappas et al further conclude that prior to their discovery, simply incorporating low boiling solvents did not increase the likelihood that an acceptable solvent system for nail enamels would be found or that one could obtain a nail enamel composition which dried in under three minutes.

Pappas et al describe their discovery as being that the use of acetone in certain weight percentages of the nail enamel composition, in combination with numerous solvents which provide acceptable viscosity, creates a consistent quick-drying solvent system which provides a nail enamel with favorable characteristics of drying time, viscosity, gloss, flexibility and durability. Thus, the Pappas et al patent teaches that the only way to make it possible to determine a proper solvent balance, to remove the uncertainty involved in determining a suitable solvent balance incorporating quick-drying characteristics, to increase the likelihood that an acceptable solvent system for nail enamels would be found, or to increase the likelihood that one could obtain a nail enamel composition which dried in under three minutes, would be to employ acetone in the solvent system. The Pappas et al patent further states that the amount of the acetone should be no less than about 4.5%, and preferably no less than 13% by weight. However, the presence of significant amounts of acetone in a nail enamel composition can lower the viscosity of the nail enamel composition to such an extent that particulate ingredients are permitted to settle, thus causing an undesirable variation in the composition. Moreover, prolonged or repeated contact of the skin with acetone can dry and defat the skin and cause dermatitis.

Although the Pappas et al patent does disclose several solvent systems which do not contain acetone, the Pappas et al patent indicates that such non-acetone solvent systems do not meet the criteria. For example, the solvent system #2 (consisting of isopropanol, ethyl acetate, n-butyl acetate, and methylchloroform) employed in Example 3 had a drying time of 3 minutes and 17 seconds under specified conditions including 40% relative humidity, or a drying time of about 4.5 to 5.0 minutes at 50–55% relative humidity. Similarly, the solvent system #3 (consisting of isopropanol, ethyl acetate, and n-butyl acetate) employed in Example 4 had a drying time of 3 minutes and 9 seconds under specified conditions including 40% relative humidity, or a drying time of about 4.5 to 5.0 minutes at 50–55% relative humidity. Also, the solvent system #9 (consisting of isopropanol, ethyl acetate, toluene, n-butyl acetate, methylene chloride, and methylchloroform) employed in Example 10 had a drying time of 3 minutes and 21 seconds under specified conditions including 37% relative humidity, or a drying time of about 4.0 to 5.0 minutes at 50–55% relative humidity.

The Pappas et al patent indicates that even when the minimum amount (4.5%) of acetone was present, the drying time was longer than desirable. Thus, in the solvent system #8 (consisting of acetone, isopropanol, ethyl acetate, toluene, n-butyl acetate, and methylchloroform) employed in Example 9, the composition had a drying time of 2 minutes under specified conditions including a low 24% relative humidity, or a drying time of about 3.0 minutes at 50–55% relative humidity. Thus, the Pappas et al patent teaches that the only way in which the desired objectives can be achieved is to employ at least 4.5% acetone in the nail polish composition.

In contrast to the express teachings of the Pappas et al patent, applicant has discovered that the objectives can be achieved without the use of any ketone, such as acetone.

Nitrocellulose, or cellulose nitrate, is a thermoplastic, non-oxidizing polymer which, when cast from a solvent solution, dries by evaporation to form a film. Nitrocellulose is a commonly employed ingredient in nail coating compositions in that nitrocellulose has good hardness, good toughness, and good resistance to abrasion. However, as nitrocellulose is relatively brittle, the adhesion of the nail coating to the nail deteriorates within a few days due to the growth of the nail so that the nail coating separates from the nail. Thus, nitrocellulose does not provide the desired long lasting adhesion of the nail coating to the nail. While the combination of a toluene-sulfonamide-formaldehyde resin with nitrocellulose in a nail coating composition is considered to improve the strength and adhesion characteristics of the nail coating composition over that offered solely by the nitrocellulose, the use of formaldehyde containing resins in a nail coating is undesirable, as the formaldehyde containing resins dry the nails and make the nails brittle. Allegeties have also been reported for resins such as arylsulfonamide/formaldehyde resins. For example, in many cases of dermatitis due to nail enamel, a toluene-sulfonamide-formaldehyde resin is the etiologic agent. Thus, there is a need for a combination of polymers which provide a nail coating composition with both the desired initial adhesion and the desired long term adhesion, while avoiding the use of formaldehyde containing polymers.

It is also desirable that the base coat protect the nails against damage from ingredients in the secondary coats as well as in the base coat, e.g., ingredients which cause drying of the nails and/or skin.

Accordingly, there is a need for a nail coating composition which is substantially free to totally free of aromatic solvents and ketones, and which is substantially free to totally free of formaldehyde containing resins, but which provides a desirable level of adhesion, both initially and long term, and which provides protection for the nail against the drying effects of solvents employed in the nail coating composition.

SUMMARY OF THE INVENTION

A nail coating composition in accordance with the present invention is substantially free to totally free of aromatic solvents, ketones, and formaldehyde containing resins, and comprises a nitrocellulose polymer, a rosin based resin, polyester, sucrose acetate isobutyrate, butyl benzyl phthalate, glyceryl tribenzoate, and a mixture of aliphatic and cycloaliphatic solvents. It is presently preferred that the nail coating composition also contain at least one vitamin, at least one moisturizer, and at least one protein. The composition is particularly useful for providing a base coat.

In one embodiment of the invention, the nail coating composition comprises nitrocellulose, maleic modified rosin based resin, polyester resin, sucrose acetate isobutyrate, butyl benzyl phthalate, glyceryl tribenzoate, at least one vitamin, at least one UV blocking agent, at least one protein, at least one moisturizer, at least one smoothing agent, at least one adhesion promoter, and a mixture of solvents, wherein all of the solvents in the nail coating composition are selected from the group consisting of alkanes having 4 to 10 carbon atoms, aliphatic esters having 3 to 10 carbon atoms, alkanols having 2 to 10 carbon atoms, cycloalkanes having 4 to 10 carbon atoms, cycloaliphatic esters having 4 to 10 carbon atoms, cycloalkanols having 4 to 10 carbon atoms, and mixtures of any two or more thereof.

In a presently preferred embodiment of the invention, the nail coating composition is free of ketones and aromatic solvents as well as formaldehyde containing resins, and comprises nitrocellulose resin, maleic modified rosin based resin, polyester resin, sucrose acetate isobutyrate, butyl benzyl phthalate, glyceryl tribenzoate, calcium panthothenate, panthenol, benzophenone-1, lanolin, aminomethoxysilane, hydrolyzed collagen, a polyether modified dimethylpolysiloxane copolymer, ethyl acetate, n-butyl acetate, n-butanol, isopropyl alcohol, and a naphthenic material, wherein the naphthenic material is a mixture of paraffins and cycloparaffins containing less than 1 percent aromatics.

DETAILED DESCRIPTION OF THE INVENTION

The term "liquid solvent" is used herein to include (a) liquid materials which are true solvents in that they dissolve the material introduced thereto, (b) liquid wetting agents, e.g., alcohols, and (c) liquid diluents, while excluding solid materials, e.g., plasticizers and secondary film forming polymers which might have some dissolving or plasticizing effect on the film forming polymer. The terms "liquid" and "solid" indicate the physical state at 20° C. and 760 mm Hg (one atmosphere) pressure. Wetting agents can be selected to provide a favorable interaction with the primary film forming polymer. The liquid diluents can be selected to provide the desired solubility characteristics which are consistent with dissolving the film forming polymer.

The nitrocellulose used as the primary film forming polymer in the nail coating composition of the present invention is a lacquer grade nitrocellulose, preferably of the "RS" or "SS" type nitrocellulose from the Aqualon Company, a division of Hercules, Incorporated, e.g., nitrocellulose RS ½ second, nitrocellulose RS ¼ second, nitrocellulose RS ⅛ second, nitrocellulose SS ½ second, etc. The RS type nitrocellulose contains about 11.2 to about 12.8 percent nitrogen, while the SS type nitrocellulose contains about 10.7 to about 11.2 percent nitrogen. The RS type nitrocellulose is available in many grades of viscosity, ranging from 18 centipoises to 500 sec. The viscosity of the nitrocellulose can be modified as desired by utilizing two nitrocelluloses of differing viscosities and varying the ratio of the two nitrocelluloses. A presently preferred nitrocellulose is a nitrocellulose ultra sen ½ sec which comprises 70 weight percent nitrocellulose and 30 weight percent isopropanol. While any suitable amount of the nitrocellulose can be used in the nail coating composition, the amount of the nitrocellulose (excluding the wetting alcohol) will generally be in the range of about 7 to about 20 weight percent, preferably will be in the range of about 8 to about 16 weight percent, and more preferably in the range of about 10 to about 15 weight percent, based on the total weight of the nail coating composition.

The rosin based resin which is used in the nail coating composition can be any suitable rosin based resin, but is preferably a maleated rosin polymer. A suitable maleated rosin polymer is the maleated rosin polymer with glycerol which is available from Union Camp Corporation as UNI-REZ® 7003 maleic modified rosin polymer. While any suitable amount of the rosin based resin can be used in the nail coating composition, the amount of the maleated rosin polymer will generally be in the range of about 1 to about 8 weight percent, preferably will be in the range of about 2 to about 6 weight percent, and more preferably in the range of about 2.5 to about 4.5 weight percent, based on the total weight of the nail coating composition. The maleated rosin polymer has high alcohol tolerance, a pale color, and promotes hardness, high gloss and adhesion.

The polyester resin employed in the nail coating composition can be any suitable polyester resin, e.g., one formed by reacting a polyhydric alcohol with a polybasic acid, e.g., phthalic acid. A presently preferred polyester is UNIPLEX 670-P polyester resin, which is available from Unitex Chemical Corporation as a clear solution of at least 70% solid polyester resin in butyl acetate solvent, having a Brookfield viscosity at 25° C. in the range of about 3200 to about 4500 cps, and which does not contain toluene, formaldehyde, or xylene. The polyester resin promotes gloss, adhesion, flexibility, wear-resistance, and water-resistance properties. While any suitable amount of the polyester can be used in the nail coating composition, the amount of the polyester (excluding the solvent) will generally be in the range of about 0.3 to about 5 weight percent, preferably will be in the range of about 0.5 to about 4 weight percent, and more preferably in the range of about 1 to about 2.5 weight percent, based on the total weight of the nail coating composition.

In general, the nail coating composition will contain at least three plasticizers, including sucrose diacetate hexaisobutyrate, butyl benzyl phthalate, and glyceryl tribenzoate. Sucrose diacetate hexaisobutyrate, $C_{40}H_{62}O_{19}$, is also known as sucrose acetate isobutyrate. Any other plasticizer suitable for use in nail coating can also be employed in the present nail coating composition. Examples of additional plasticizers include organic phthalates, organic adipates, and organic phosphates, e.g., butyl benzyl phthalate, camphor, dibutyl phthalate, tricresyl phosphate, diethyl phthalate, tributyl phosphate, dibutyl glycolate, dioctyl phthalate, butyl stearate, triphenyl phosphate, dibutyl ether phthalate, acetyl tributyl citrate, glyceryl triacetate, glyceryl tribenzoate, dicyclohexyl phthalate, ethylene glycol dibenzoate, and mixtures of any two or more thereof. Each of sucrose diacetate hexaisobutyrate, butyl benzyl phthalate, and glyceryl tribenzoate can be employed in any suitable amount, but each will in general be employed in an amount in the range of about 0.5 to about 8 weight percent, and preferably in an amount in the range of about 1 to about 6 weight percent, based on the total nail coating composition.

In general, the nail coating composition will contain at least one suitable vitamin, preferably a member of the vitamin B family. A presently preferred vitamin is d-panthenol, $C_9H_{19}NO_4$, also known as Pro-Vitamin B5 or d(+)-pantothenyl alcohol, which is available from Roche Vitamins and Fine Chemicals as dex-Panthenol. Each vitamin can be present in the nail coating composition in any suitable amount, but each will generally be in the range of about 0.001 to about 0.02 weight percent, and preferably will be in the range of about 0.003 to about 0.01 weight percent, based on the total weight of the nail coating composition.

In general, the nail coating composition will contain at least one UV blocking agent, and any suitable UV blocker can be employed. However, it is presently preferred to employ at least two UV blockers having different ranges of UV wavelength blockage so as to extend the protection against UV radiation. Any suitable amount of the UV blockers can be employed, but the amount of each UV blocker will generally be in the range of about 0.001 to about 0.2 weight percent, and preferably will be in the range of about 0.01 to about 0.05 weight percent, based on the total weight of the nail coating composition. The presently preferred UV blocker is benzophenone-1.

In general, the nail coating composition will contain at least one protein, e.g., collagen, and at least one moisturizer, e.g., lanolin. In a presently preferred base coat composition, the protein and lanolin is provided in the form of PROTO-LAN 30, a water soluble, collagen/lanolin oil base emollient containing propylene glycol, lanolin oil, and hydrolyzed collagen, available from Maybrook Inc., and recommended for use in hair and skin care products. This material moisturizes the skin, leaving a soft after-feel, and is beneficial to dry, chapped skin. It also improves dry-down properties of alcoholic systems and mitigates the harsh effect of the alcohol. Each of the protein and the moisturizer can be employed in the nail coating composition in any suitable amount, but each will generally be in the range of about 0.001 to about 0.5 weight percent, and preferably will be in the range of about 0.01 to about 0.1 weight percent, based on the total weight of the nail coating composition.

The solvents in the nail coating composition area mixture of acyclic aliphatic and cycloaliphatic solvents. It is presently preferred that the solvent for the film forming polymers be a mixture of acyclic aliphatic liquid solvents and cycloaliphatic liquid solvents, wherein the acyclic aliphatic liquid solvents can be linear or branched aliphatic compounds, and wherein the cycloaliphatic liquid solvents can be simple cycloaliphatic compounds without any branches on the rings, or branched cycloaliphatic compounds, e.g., alkylcycloaliphatic compounds, dialkylcycloaliphatic compounds, trialkylcycloaliphatic compounds, tetraalkylcycloaliphatic compounds, etc.

Suitable aliphatic solvents include alkanes having 4 to 10 carbon atoms per molecule, aliphatic esters having 3 to 10 carbon atoms per molecule, alkanols having 2 to 10 carbon atoms per molecule, e.g., n-butane, isobutane, n-pentane, isopentane, hexane, heptane, isoheptane, octane, 3,3-dimethyl hexane, 3-ethyl hexane, nonane, 2,2,3-trimethyl hexane, 2-methyl octane, 3-ethyl-2-methyl hexane, 2,3-dimethyl octane, decane, methyl propionate, methyl acetate, ethyl acetate, n-propyl acetate, n-butyl acetate, isobutyl acetate, sec-butyl acetate, tert-butyl acetate, 1,1-dimethyl butyl acetate, n-propyl formate, ethyl propionate, hexyl acetate, 3-ethyl-3-pentyl acetate, octyl acetate, 2-ethyl hexyl acetate, ethanol, n-propanol, isopropanol, n-butanol, n-pentanol, n-hexanol, n-heptanol, 3-methyl 3-hexanol, 2-ethyl 3-hexanol, n-octanol, n-decanol, and mixtures of any two or more thereof. The presently preferred aliphatic esters are the acyclic hydrocarbyl esters having 3 to 6 carbon atoms per molecule, and the presently preferred alkanols are those having 3 to 6 carbon atoms per molecule. While the alkanes having 4 to 6 carbon atoms per molecule can be utilized in the invention, the presently preferred alkanes are those having 7 to 10 carbon atoms per molecule, and the more preferred are those having 8 to 9 carbon atoms per molecule.

Suitable cycloaliphatic solvents include cycloalkanes having 4 to 10 carbon atoms per molecule, cycloaliphatic esters having 4 to 10 carbon atoms per molecule, cycloalkanols having 4 to 10 carbon atoms per molecule, e.g., cyclobutane, cyclopentane, methyl cyclobutane, cyclohexane, ethyl cyclobutane, methyl cyclopentane, ethyl cyclopentane, propyl cyclopentane, 1,1,2-trimethyl cyclopentane, 1,1-dimethyl cyclohexane, 1,2-dimethyl cyclohexane, 1,3-dimethyl cyclohexane, 1,4-dimethyl cyclohexane, ethyl cyclohexane, propyl cyclohexane, isopropyl cyclohexane, 1,1,3-trimethyl cyclohexane, 1-methyl-4-ethyl cyclohexane, n-butyl cyclohexane, isobutyl cyclohexane, cyclobutanol, cyclobutylcarbinol, cyclopentanol, naphthenes, and mixtures of any two or more thereof. The presently preferred cycloalkanols are those having 4 to 6 carbon atoms per molecule. Similarly, the presently preferred cycloaliphatic esters are those having 4 to 6 carbon atoms per molecule. However, while the cycloalkanes having 4 to 6 carbon atoms per molecule can be employed in the invention, the presently preferred cycloalkanes are the branched and unbranched cycloalkanes having 7 to 10 carbon atoms per molecule, and the more preferred cycloalkanes are those having 8 to 9 carbon atoms per molecule.

Each of the solvents can be employed in any suitable amount. In general, the total amount of solvents in the nail coating composition will be in the range of about 55 to about 85 weight percent, and preferably will be in the range of about 62 to about 82 weight percent, and more preferably in the range of about 66 to about 80 weight percent, based on the total weight of the nail coating composition. In general, the cycloaliphatic solvents will constitute from about 0.8 to about 20 weight percent, preferably from about 1.5 to about 15 weight percent, and more preferably from about 2 to about 10 weight percent, based on the total weight of the nail coating composition. A presently preferred solvent mixture (including the solvents present in the polymeric ingredients) comprises ethyl acetate in the range of about 25 to about 45 weight percent, preferably in the range of about 30 to about 40 weight percent; n-butyl acetate in the range of about 15 to about 32 weight percent, preferably in the range of about 20 to about 28 weight percent; n-butanol in the range of about 0.5 to about 10 weight percent, preferably in the range of about 1 to about 5 weight percent; isopropanol in the range of about 1 to about 12 weight percent, preferably in the range of about 3 to about 10 weight percent; and napthenic material in an amount in the range of about 1 to about 20 weight percent, and preferably in the range of about 2 to about 10 weight percent, with the napthenic material having an alkane content in the range of about 10 to about 90 volume percent and a cycloalkane content in the range of about 90 to about 10 volume percent; with each of the weight percentages being based on the total weight of the nail coating composition.

Many of the commercially available naphthenic materials are petroleum refinery product streams composed of acyclic alkanes and cycloalkanes (naphthenes) having from 6 to 10 carbon atoms per molecule, the acyclic alkanes constituting from about 10 to about 90 volume percent of the naphthentic material and the cycloalkanes constituting about 90 to about 10 volume percent of the naphthenic material, with the aromatic content being less than 1 volume percent. It is presently preferred that at least 70, more preferably at least 80, and even more preferably at least 90, volume percent of the naphthenic material be acyclic alkanes and cycloalkanes containing 8 to 9 carbon atoms per molecule, with the alkane content being in the range of about 25 to about 90 volume percent and more preferably in the range of about 30 to 50 volume percent, the cycloalkane content being in the range of about 75 to about 10 volume percent and more preferably in the range of about 70 to about 50 volume percent, and the aromatic content being less than about 0.1 volume percent and more preferably less than about 0.01 volume percent of the naphthenic material. The naphthenic material can be a Naphtholite™ naphthenic material which is available from Union 76 Chemicals as a mixture of paraffins and cycloparaffins containing less than 1 percent aromatics, with the paraffin content being in the range of about 37 to about 50 percent and the cycloparaffin content being in the range of about 62 to about 49 percent, with at least about 90 volume percent of the paraffins and cycloparaffins having 8 to 9 carbon atoms per molecule. The naphthenic material can be a KERMAC™ VM&P Naphtha, Rule 66, which is available from Kerr-McGee Refining Corporation as a light aliphatic solvent naphtha, containing a mixture of acyclic paraffins and cycloparaffins and less than 1 percent aromatics. The naphthenic material can be a light aliphatic solvent naphtha available from Shell Chemical Company as Shell VM&P Naphtha HT™, which is a complex combination of aliphatic hydrocarbons and cycloaliphatic hydrocarbons containing 8 to 9 carbon atoms per molecule with a high naphthene content and less than 0.01 volume percent aromatic hydrocarbons.

In order to provide the desired characteristics of flow and level, the nail coating composition can contain a smoothing agent. The smoothing agent reduces friction, improves the flow of the nail coating composition during application, and improves the levelness and gloss of the surface of the nail coating composition upon drying. Suitable smoothing agents include silicone polymers and copolymers, polyamides, polyacrylamides, and polycarboxylic acids, and mixtures of any two or more thereof. Any suitable amount of smoothing agent can be employed, but the amount will generally be in the range of about 0.01 to about 2 weight percent, preferably in the range of about 0.1 to about 1 weight percent, based on the total weight of the nail coating composition. The presently preferred smoothing agent is a polysiloxane copolymer.

In order to provide the desired characteristics of adhesion, the nail coating composition can contain an adhesion promoter. The adhesion promoter improves the adhesion of the nail coating to the nail or to any previously applied coats. Any suitable amount of adhesion promoter can be employed, but the amount will generally be in the range of about 0.1 to about 5 weight percent, and preferably will be in the range of about 0.5 to about 3 weight percent, based on the total weight of the nail coating composition. Examples of suitable adhesion promoters which can be employed include sucrose benzoates, sucrose acetate isobutyrates, and aminoalkoxysilanes, with aminomethoxysilane being presently preferred.

In order to facilitate the introduction of the smoothing agent and the adhesion promoter into the nail coating composition, it is desirable that these components first be dispersed in a suitable solvent, preferably an alkanol having 2 to 6 carbon atoms, and the resulting solution then be added to the solution of the film forming polymer in its mixture of solvents. The presently preferred solvent for the smoothing agent and the adhesion promoter is isopropyl alcohol.

The nail coating composition can be applied as a base coat over natural or synthetic nails to act as a primer for pigmented nail polishes or nail clears. The base coat dries to the touch in less than two minutes, and a secondary coat can then be applied to the base coat; this permits the concentration of solvents at the interface of the base coat and the secondary coat to be reduced sufficiently so that adequate adhesion of the secondary coat to the base coat is achieved. This base coat provides excellent flexibility, excellent initial adhesion to the bare nail as well as excellent adhesion for at least seven days, good water resistance, excellent hardness, good strengthening, good holdout (ability of coating to provide a glossy, non-porous surface), good UV protection, calcium nutrient for the nails, and good epidermal moisturizing.

EXAMPLE I

A base nail coating composition, comprising nitrocellulose, maleic modified resin, toluenesulfonamide and a formaldehyde containing resin as the film forming polymers, and butyl benzyl phthalate and glyceryl tribenzoate as the plasticizers, was prepared with the following ingredients in the indicated concentrations:

| INGREDIENT | WEIGHT % |
| --- | --- |
| Ethyl acetate | 34.78 |
| N-butyl-acetate | 23.19 |
| N-butanol | 3.52 |
| Naphthenic material | 4.45 |
| Isopropanol | 2.34 |
| Nitrocellulose | 16.40 |
| Maleic Modified rosin polymer | 1.17 |
| Toluenesulfonamide | 4.68 |
| Formaldehyde resin | 2.58 |
| Butyl benzyl phthalate | 3.51 |
| Glyceryl tribenzoate | 1.87 |
| Dex-Panthenol | 0.006 |
| D-calcium panthothenate | 0.006 |

-continued

| INGREDIENT | WEIGHT % |
|---|---|
| Protein and Lanolin | 0.059 |
| Benzophenone-1 | 0.023 |
| Polysiloxane copolymer | 0.234 |
| Aminomethoxysilane | 1.17 |
| Total | ~100 |

EXAMPLE II

A base nail coating composition, comprising nitrocellulose and maleic modified resin as the film forming polymers, and sucrose acetate isobutyrate, butyl benzyl phthalate and glyceryl tribenzoate as the plasticizers, was prepared with the following ingredients in the indicated concentrations:

| INGREDIENT | WEIGHT % |
|---|---|
| Ethyl acetate | 35.17 |
| N-butyl acetate | 23.48 |
| N-butanol | 3.02 |
| Naphthenic material | 5.03 |
| Isopropanol | 2.61 |
| Nitrocellulose | 15.65 |
| Maleic Modified rosin polymer | 3.56 |
| Sucrose acetate isobutyrate | 2.37 |
| Butyl benzyl phthalate | 3.56 |
| Glyceryl tribenzoate | 3.79 |
| Dex-Panthenol | 0.006 |
| D-calcium panthothenate | 0.006 |
| Protein and Lanolin | 0.059 |
| Benzophenone-1 | 0.024 |
| Polysiloxane copolymer | 0.23 |
| Aminomethoxysilane | 1.42 |
| Total | ~100 |

EXAMPLE III

A base nail coating composition, comprising nitrocellulose, maleic modified resin, and polyester as the film forming polymers, and sucrose acetate isobutyrate and butyl benzyl phthalate as the plasticizers, was prepared with the following ingredients in the indicated concentrations:

| INGREDIENT | WEIGHT % |
|---|---|
| Ethyl acetate | 35.73 |
| N-butyl acetate | 23.84 |
| N-butanol | 3.07 |
| Naphthenic material | 5.11 |
| Isopropanol | 2.65 |
| Nitrocellulose | 16.13 |
| Maleic Modified rosen polymer | 3.61 |
| Polyester | 2.05 |
| Sucrose acetate isobutyrate | 2.41 |
| Butyl benzyl phthalate | 3.61 |
| Dex-Panthenol | 0.006 |
| D-calcium panthothenate | 0.006 |
| Protein and Lanolin | 0.059 |
| Benzophenone-1 | 0.025 |
| Polysiloxane copolymer | 0.24 |
| Aminomethoxysilane | 1.45 |
| Total | ~100 |

EXAMPLE IV

A base nail coating composition, comprising nitrocellulose, maleic modified resin, and polyester as the film forming polymers, and sucrose acetate isobutyrate, butyl benzyl phthalate and glyceryl tribenzoate as the plasticizers, was prepared with the following ingredients in the indicated concentrations:

| INGREDIENT | WEIGHT % |
|---|---|
| Ethyl acetate | 34.40 |
| N-butyl acetate | 22.96 |
| N-butanol | 2.95 |
| Naphthenic material | 4.92 |
| Isopropanol | 2.55 |
| Nitrocellulose | 15.53 |
| Maleic Modified rosin polymer | 3.48 |
| Polyester | 1.98 |
| Sucrose acetate isobutyrate | 2.32 |
| Butyl benzyl phthalate | 3.48 |
| Glyceryl tribenzoate | 3.71 |
| Dex-Panthenol | 0.006 |
| D-calcium panthothenate | 0.006 |
| Protein and Lanolin | 0.057 |
| Benzophenone-1 | 0.024 |
| Polysiloxane copolymer | 0.23 |
| Aminomethoxysilane | 1.39 |
| Total | ~100 |

SOLVENTS

In the compositions of Examples I–IV, the ethyl acetate and the n-butyl acetate are obtainable from Eastman Chemical Company. The n-butyl acetate is also available from Hoechst Celanese as n-butyl acetate, urethane grade. The naphthenic material is a mixture of acyclic paraffins and cycloparaffins having from 7 to 10 carbon atoms per molecule, is at least substantially free of aromatics, and is available as KERMAC VM&P Naphtha, Rule 66, light aliphatic solvent naphtha from Kerr-McGee Refining Corporation. The isopropanol is available from Exxon Chemical Americas.

FILM FORMERS

In the compositions of Examples I–IV, the nitrocellulose is nitrocellulose ultra sen ½ sec, which is wet with 30 weight percent isopropanol, available from the Aqualon Company.

The toluenesulfonamide of Example I is available from the Unitex Chemical Corporation as UNIPLEX 171. The formaldehyde resin of Example I is available from the Unitex Chemical Corporation as UNIPLEX 600.

In the compositions of Examples I–IV, the maleic modified rosin polymer is UNI-REZ® 7003 maleic modified rosin polymer available from the Union Camp Corporation, which is recommended for use with nitrocellulose in sanding sealers, wood lacquers and fillers, and in gravure inks.

In the compositions of Examples III and IV, the polyester is UNIPLEX 670-P polyester, available from Unitex Chemical Corporation as a solution of the polyester resin in butyl acetate, and is recommended for use in nitrocellulose based fingernail enamels to impart excellent adhesion, wear, and water-resistant properties.

PLASTICIZERS

In the compositions of Example III and IV, the sucrose acetate isobutyrate is available as EASTMAN SAIB, Industrial Grade, from Eastman Chemical Company and is recommended as a plasticizer.

In the compositions of Examples I–IV, the butyl benzyl phthalate is Santicizer® 160 plasticizer, available from Monsanto Company.

In the compositions of Examples I, II, and IV, the glyceryl tribenzoate is a solid polyol benzoate modifier available as UNIPLEX 260 glyceryl tribenzoate from Unitex Chemical Corporation, and is recommended as a plasticizer for polyvinyl acetate-based adhesives, cellophane coatings, and nitrocellulose coatings where it promotes heat-sealability and adhesion, creates a moisture barrier and resists oil/water extraction.

VITAMINS, PROTEIN and LANOLIN

In the compositions of Examples I–IV, each of the dex-panthenol and the d-calcium panthothenate is a member of the vitamin B5 family, and each is available from Roche Vitamins and Fine Chemicals, a member of the Roche Group.

In the compositions of Examples I–IV, the protein and lanolin is PROTO-LAN 30, a water soluble, collagen/lanolin oil base emollient containing propylene glycol, lanolin oil, and hydrolyzed collagen, available from Maybrook Inc., and recommended for use in hair and skin care products.

OTHER ADDITIVES

In the compositions of Examples I–IV, the benzophenone-1 is Lowilite® 24 2,4-dihydroxyphenyl, available from Great Lakes Chemical Corporation, and is recommended as an ultraviolet stabilizer.

In the compositions of Examples I–IV, the polysiloxane copolymer is BYK-301 ethylene glycol monobutyl ether solution, a solution of a polyether modified dimethylpolysiloxane copolymer, available from BYK-Chemie U.S.A., and recommended for use as a paint additive.

In the compositions of Examples I–IV, the aminomethoxysilane is Dow Corning® Z-6040 silane, which contains approximately 99 weight percent glycidoxypropyl trimethoxysilane and less than 2 weight percent methanol, available from Dow Corning Corporation.

PROCEDURE

In each of Examples I–IV, the ethyl acetate, n-butyl acetate, n-butanol, and naphthenic material were mixed together in a first container to form a mixed solvent. The benzophenone-1 and the d-calciumpanthothenate were added to the mixed solvent and stirred for approximately five minutes; after which the film forming polymers, the plasticizers, and the dex-panthenol were added to the stirred mixture, and the stirring continued to obtain a resin/solvent mixture. In a separate covered container, the isopropanol, the polysiloxane copolymer, the aminomethoxysilane, the butyl benzyl phthalate, and the protein and lanolin were mixed together for approximately ten minutes, and the resulting mixture was then added to the resin/solvent mixture and blended together to form the nail coating composition.

COMPARISON

The base nail coating compositions of Examples I–IV were tested for long term adhesion, with the following results:

| BASE COATING COMPOSITION | TERM OF GOOD ADHESION |
| --- | --- |
| Example I | 7+ days |
| Example II | 3–4 days |
| Example III | 3–4 days |
| Example IV | 7+ days |

Thus, the base nail coating composition of Example IV, based on the combination of nitrocellulose, maleic modified rosin polymer, and polyester as the film forming polymers, and the combination of sucrose acetate isobutyrate, butyl benzyl phthalate and glyceryl tribenzoate as the plasticizers, provided a long lasting adhesive which was as good as that of the base nail coating composition of Example I, based on nitrocellulose and a formaldehyde containing polymer, but without the presence of the detrimental formaldehyde containing polymer.

On the other hand, the base nail coating composition of Example II, which contained the combination of the three plasticizers (sucrose acetate isobutyrate, butyl benzyl phthalate and glyceryl tribenzoate) of the base nail coating composition of Example IV but only two of the film forming polymers (nitrocellulose and maleic modified rosin polymer) of the base nail coating composition of Example IV, had a substantially shorter term of good adhesion, as did the base nail coating composition of Example III, which contained the combination of the three film forming polymers (nitrocellulose, maleic modified rosin polymer, and polyester) of Example IV but only two of the plasticizers (sucrose acetate isobutyrate and butyl benzyl phthalate) of Example IV. Thus, the desired long term adhesion was achieved only with the combination of the three plasticizers (sucrose acetate isobutyrate, butyl benzyl phthalate and glyceryl tribenzoate) and the combination of the three film forming polymers (nitrocellulose, maleic modified resin, and polyester).

EXAMPLE V

A base nail coating composition, prepared from the following ingredients of the base nail coating composition of Example IV: ethyl acetate, n-butyl acetate, naphthenic material, n-butanol, isopropanol, nitrocellulose, benzophenone-1, butyl benzyl phthalate, glyceryl tribenzoate, d-calcium panthothenate, dex-panthenol, protein and lanolin, (i.e., omitting the maleic modified rosin polymer, polyester, sucrose acetate isobutyrate, polysiloxane copolymer, and aminomethoxysilane) is applied as a base coat. This base coat exhibits reduced water resistance, reduced adhesion, less hardness, less strengthening, reduced holdout, and reduced flexibility, as compared with the base coat provided by the composition of Example IV. This indicates the advantages of including the maleic modified rosin polymer, polyester, sucrose acetate isobutyrate, polysiloxane copolymer, and aminomethoxysilane in the base nail coating composition of Example IV.

EXAMPLE VI

A base nail coating composition, prepared from the same ingredients of the base nail coating composition of Example V except for the omission of the glyceryl tribenzoate, is applied as a base coat. This base coat is brittle in comparison to the base coat provided by the composition of Example V, as well as exhibiting the above noted deficiencies of the base nail coating composition of Example V when compared with the base nail coating composition of Example IV.

EXAMPLE VII

A base nail coating composition, prepared from the same ingredients of the base nail coating composition of Example VI except for the omission of the butyl benzyl phthalate, dex-Panthenol, D-calcium panthothenate, protein and lanolin, and benzophenone-1, is applied as a base coat. In addition to being brittle in comparison to the base coat provided by the composition of Example V, and exhibiting the above noted deficiencies of the base nail coating composition of Example V when compared with the base nail coating composition of Example IV, this base nail coating composition exhibits loss of UV light protection, loss of calcium nutrient, loss of skin nutrient, loss of lanolin epidermal moisturizer, loss of emollient, and loss of protein skin nutrient when compared with the base nail coating composition of Example IV.

Reasonable variations in and modifications to the invention are possible within the scope of the foregoing description and the appended claims.

That which is claimed is:

1. A nail coating composition comprising nitrocellulose, a rosin polymer, polyester, sucrose acetate isobutyrate, butyl benzyl phthalate, glyceryl tribenzoate, and a mixture of aliphatic and cycloaliphatic solvents, the composition being substantially free to totally free of aromatic solvents, ketones, and formaldehyde containing resins.

2. A composition in accordance with claim 1, further comprising at least one vitamin, at least one moisturizer, and at least one protein.

3. A composition in accordance with claim 2, further comprising at least one UV blocking agent, at least one smoothing agent, and at least one adhesion promoter.

4. A composition in accordance with claim 3, wherein the rosin polymer is a maleic modified rosin based resin.

5. A composition in accordance with claim 4, wherein said at least one UV blocking agent comprises benzophenone-1.

6. A composition in accordance with claim 4, wherein said at least one smoothing agent comprises a polysiloxane copolymer.

7. A composition in accordance with claim 4, wherein said at least one adhesion promoter comprises aminomethoxysilane.

8. A composition in accordance with claim 4, wherein all of the solvents in the composition are selected from the group consisting of alkanes having 4 to 10 carbon atoms, aliphatic esters having 3 to 10 carbon atoms, alkanols having 2 to 10 carbon atoms, cycloalkanes having 4 to 10 carbon atoms, cycloaliphatic esters having 4 to 10 carbon atoms, cycloalkanols having 4 to 10 carbon atoms, and mixtures of any two or more thereof.

9. A composition in accordance with claim 1, wherein the rosin polymer is a maleic modified rosin polymer.

10. A composition in accordance with claim 1, further comprising at least one UV blocking agent, at least one smoothing agent, and at least one adhesion promoter.

11. A composition in accordance with claim 10, wherein said at least one UV blocking agent comprises benzophenone-1.

12. A composition in accordance with claim 10, wherein said at least one smoothing agent comprises a polysiloxane copolymer.

13. A composition in accordance with claim 10, wherein said at least one adhesion promoter comprises aminomethoxysilane.

14. A composition in accordance with claim 1, wherein all of the solvents in the composition are selected from the group consisting of alkanes having 4 to 10 carbon atoms, aliphatic esters having 3 to 10 carbon atoms, alkanols having 2 to 10 carbon atoms, cycloalkanes having 4 to 10 carbon atoms, cycloaliphatic esters having 4 to 10 carbon atoms, cycloalkanols having 4 to 10 carbon atoms, and mixtures of any two or more thereof.

15. A nail coating composition consisting essentially of nitrocellulose, a rosin polymer, polyester, sucrose acetate isobutyrate, butyl benzyl phthalate, glyceryl tribenzoate, at least one vitamin, at least one moisturizer, and at least one protein, at least one UV blocking agent, at least one smoothing agent, at least one adhesion promoter, and a mixture of aliphatic and cycloaliphatic solvents, the composition being substantially free to totally free of aromatic solvents, ketones, and formaldehyde containing resins.

16. A nail coating composition comprising film forming polymers consisting essentially of nitrocellulose, a rosin polymer, and polyester; plasticizers consisting essentially of sucrose acetate isobutyrate, butyl benzyl phthalate, and glyceryl tribenzoate; and solvents consisting essentially of aliphatic and cycloaliphatic solvents.

17. A nail coating composition in accordance with claim 16, further comprising at least one vitamin, at least one moisturizer, and at least one protein.

18. A nail coating composition in accordance with claim 16, further comprising at least one UV blocking agent, at least one smoothing agent, and at least one adhesion promoter.

19. A composition in accordance with claim 16, wherein all of the solvents in the composition are selected from the group consisting of alkanes having 4 to 10 carbon atoms, aliphatic esters having 3 to 10 carbon atoms, alkanols having 2 to 10 carbon atoms, cycloalkanes having 4 to 10 carbon atoms, cycloaliphatic esters having 4 to 10 carbon atoms, cycloalkanols having 4 to 10 carbon atoms, and mixtures of any two or more thereof.

20. A composition which is free of ketones and aromatic solvents as well as formaldehyde containing resins, said composition consisting essentially of: nitrocellulose, maleic modified rosin polymer, polyester, sucrose acetate isobutyrate, butyl benzyl phthalate, glyceryl tribenzoate, calcium panthothenate, panthenol, benzophenone-1, aminomethoxysilane, lanolin, hydrolyzed collagen, a polyether modified dimethylpolysiloxane copolymer, ethyl acetate, n-butyl acetate, n-butanol, isopropyl alcohol, and a naphthenic material, wherein the naphthenic material is a mixture of paraffins and cycloparaffins containing less than 1 percent aromatics.

* * * * *